United States Patent [19]
Mortenson et al.

[11] Patent Number: 5,253,276
[45] Date of Patent: Oct. 12, 1993

[54] DUAL-LONGITUDINAL-MODE ULTRASONIC TESTING

[75] Inventors: Steven C. Mortenson, San Jose, Calif.; Brad M. Dummer, Roswell, Ga.

[73] Assignee: General Electric Company, San Jose, Calif.

[21] Appl. No.: 985,744

[22] Filed: Dec. 4, 1992

Related U.S. Application Data

[63] Continuation of Ser. No. 771,373, Oct. 2, 1991, abandoned.

[51] Int. Cl.$^5$ .......................... G21C 17/003
[52] U.S. Cl. ..................... 376/249; 376/245; 376/252; 73/620; 73/621; 73/622; 73/624; 73/629
[58] Field of Search ............. 326/245, 249, 252; 73/620, 621, 622, 624, 628, 629

[56] References Cited

U.S. PATENT DOCUMENTS

| | | | |
|---|---|---|---|
| 3,302,453 | 2/1967 | Wood et al. | 73/67.7 |
| 3,934,457 | 1/1976 | Clark et al. | 73/67.85 |
| 4,435,984 | 3/1984 | Gruber | 73/628 |
| 4,474,064 | 10/1984 | Naruse et al. | 73/622 |
| 4,570,487 | 2/1986 | Gruber | 73/624 |
| 4,577,507 | 3/1986 | Jestrich et al. | 73/640 |
| 4,640,131 | 2/1987 | Kröning et al. | 73/600 |
| 4,680,967 | 7/1987 | Rost | 73/628 |

OTHER PUBLICATIONS

Krautkraemer, Joseph & Herbert. *Ultrasonic Testing of Materials* (New York: Springer Verlag, 4th ed.), pp. 31-34.

Bennett, William F. and Greer, Amos S. "Access Engineering and Other Related Problems of Nuclear Power Plants." ASMT Materials Evaluation, Sep. 1975, pp. 227-231.

NUREG-0619, *BWR Feedwater Nozzle and Control Rod Drive Return Line Nozzle Cracking*, U.S. Nuclear Regulatory Commission, p. 15.

*Primary Examiner*—Peter A. Nelson
*Assistant Examiner*—Chrisman D. Carroll
*Attorney, Agent, or Firm*—John S. Beulick

[57] ABSTRACT

A method of ultrasonic inspection of a reactor nozzle involves positioning emitter and receiver transducers on the exterior vessel wall near the nozzle. The emitter transducer is positioned and oriented so that it generates both primary longitudinal and transverse beams. The primary longitudinal beam is directed at the inner radius of the nozzle. The transverse beam is directed toward the interior vessel wall at an angle of about 30° to the normal. Most of the energy of the transverse beam is converted to a secondary longitudinal beam also directed toward the inner radius of the nozzle. The receiver transducer is positioned on the exterior vessel wall about 4" from the emitter transducer so as to be able to detect reflections of both the primary and second longitudinal beams from any potential defect in the nozzle volume adjacent the inner radius.

6 Claims, 4 Drawing Sheets

DUAL-LONGITUDINAL-MODE ULTRASONIC TESTING

This is a continuation of copending U.S. patent application Ser. No. 07/771,373, filed Oct. 2, 1991, now abandoned.

BACKGROUND OF THE INVENTION

The present invention relates to non-destructive testing and, more particularly, to ultrasonic inspection of material bodies for defects. A major objective of the present invention is to provide for economical and effective inspection of nuclear reactor vessel nozzles.

Nuclear reactors must be routinely inspected for defects that could result in leakage from a reactor vessel if left undetected and allowed to grow. One relatively economical and effective inspection method uses ultrasonic examination. Generally, ultrasonic inspection involves directing an ultrasonic beam into a volume to be inspected and monitoring reflections of the beam. The location of a boundary causing a reflection can be determined from the time between pulse transmission and the detection of the reflection. A reflection from within the material body may be an indication of a defect. Further ultrasonic testing from successive transducer positions can confirm and characterize a defect.

Nuclear reactor nozzles pose a severe challenge to ultrasound techniques. In particular, the physics of ultrasound makes it difficult to provide reliable inspections of the inner radii of reactor nozzles. For example, one type of boiling water reactor (BWR) has several feedwater return nozzles disposed about the circumference of a reactor vessel slightly above the reactor core. The inner radius of such a nozzle can be subject to considerable thermal stress, mechanical fatigue, and potential cracking. Ideally, this inner radius would be inspected from inside the reactor or inside the nozzle. However, the required reactor disassembly, the requirement of removing reactor water, and the potential exposure to radiation from the core make this undesirable.

Economical ultrasound testing requires that the interior defects be inspected from the exterior of the vessel. This means that the transducer that emits the ultrasound beam and the transducer that detects the reflections (which are usually the same transducer, but can be different transducers) must be on the vessel exterior. The emitting transducer must be positioned and oriented to direct energy to a volume to be inspected. The receiving transducer must be positioned and oriented to detect reflections from potential defects in that volume. Since defects are typically of unknown dimensions and orientation, it is preferable to expose them to diverse ultrasound beams to increase the likelihood of detection of defects and to enhance characterization of detected defects.

Standard ultrasound techniques allow effective inspection of certain geometries. For example, defects at the interior wall of a cylinder can be effectively detected from the cylinder's exterior. Nozzle bores, for example, have a cylindrical geometry, and are thus subject to reliable inspection. However, volumes at the nozzle inner radius and adjacent bore are accessible from fewer positions so that defects can be "illuminated" from fewer angles. Thus, defects more readily escape detection and are more difficult to characterize. In particular, radially-oriented defects, which experience shows to be common, are difficult to detect using conventional techniques. Accordingly, resort has been made to alternative inspection methods, including dye penetration techniques. However, these are much less convenient and economical. What is needed is an effective method for ultrasonically inspecting reactor nozzles from the vessel exterior.

SUMMARY OF THE INVENTION

In accordance with the present invention, an emitter transducer means directs an ultrasound beam at an angle less than the first critical angle for a material body. This produces primary longitudinal and transverse ultrasound beams within the material body. The primary longitudinal beam is directed within the material body to the volume to be inspected. The transverse beam is directed within the material body to a second surface so as to generate upon reflection a secondary longitudinal beam directed to the inspection volume. Preferably, the angle of incidence of the transverse beam on the second surface is between 25° and 35°. The inspection volume is thus illuminated from two different directions by longitudinal ultrasound beams. A receiver transducer means is positioned to detect reflections from the primary and secondary longitudinal beams from a potential defect within the inspection volume. Once the emitter transducer is activated, the receiver transducer can detect the reflection of the primary longitudinal beam and then the reflection of the secondary longitudinal beam. In addition to allowing inspection of more volume of the nozzle than conventional techniques, the reflection of a second beam can provide confirmation of a detected flaw, increasing reliability.

In practice, emitter and receiver transducers can be mounted a fixed distance apart and at fixed relative orientations. The transducers can then be moved in unison along a predetermined path, closed or open. A series of ultrasound pulses can be emitted at successive positions, and the resulting reflections can be monitored and recorded. The data so obtained can be analyzed collectively to obtain defect signatures allowing precise characterization of defects.

The present invention is contrasted with the prevailing ultrasound technique of directed ultrasound energy at an angle between the first and second critical angles for the material body. This approach rejects the longitudinal mode, admitting only the transverse mode into the body. This approach was designed to minimize "spurious" detections, simplifying analysis.

The present invention provides for improved inspection of certain geometries. Of particular interest herein is the inspection of reactor nozzles. However, the advantage generalizes to other inspection objects having parallel external and internal surfaces and a volume adjacent to a non-parallel interior surface. The method establishes a virtual transducer at the parallel interior surface, serving to illuminate defects at the non-parallel surface from a second direction. Thus, the present invention permits reactor nozzles to be inspected from the vessel exterior, avoiding a requirement of physical access to the reactor interior for testing. The external testing saves cost, time, and radiation exposure. The invention has been found to be particularly effective at detecting radial flaws, which are of concern in reactor nozzle interiors. These and other features and advantages of the present invention are apparent from the description below with reference to the following drawings.

DESCRIPTION OF THE PREFERRED EMBODIMENTS

Figure 1:
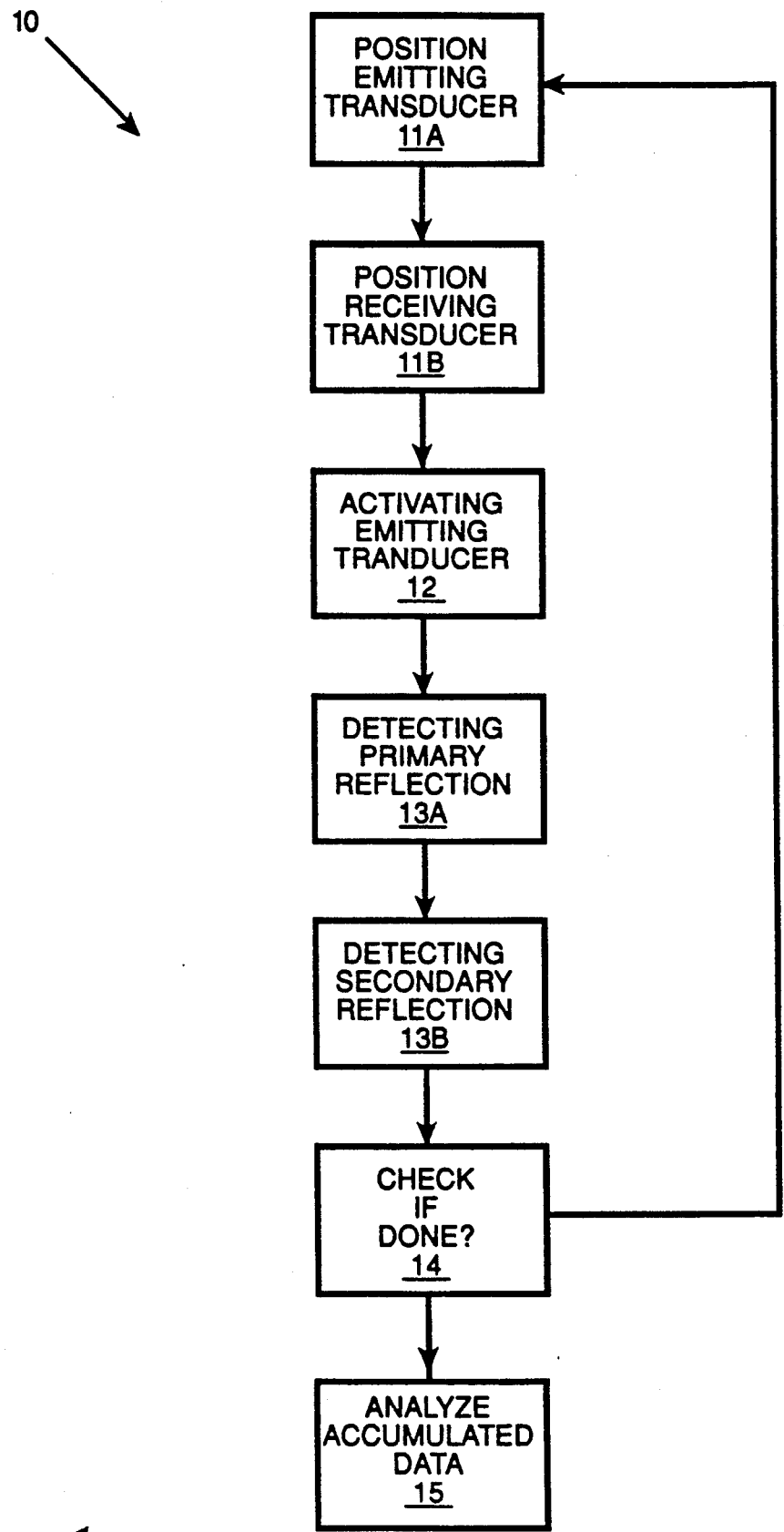
FIG. 1 is a flow chart of a method in accordance with the present invention.

In accordance with the present invention, an ultrasonic inspection method 10, flow charted in FIG. 1, provides for detection of defects in certain heretofore difficult-to-inspect geometries. Method 10 involves positioning and orienting an emitter transducer means at step 11A and positioning and orienting a receiver transducer means at step 11B. Preferably, the two transducers are rigidly coupled so that steps 11A and 11B are performed concurrently.

The emitter transducer means is positioned so that a volume to be inspected is intersected by two different beams. The volume is to be intersected by a primary longitudinal (mode) beam directly, and by a secondary longitudinal beam. The secondary longitudinal beam results from the conversion of a primary transverse beam upon reflection. The position and orientation of the emitter transducer means is thus determined by the surface at which the emitter transducer means is located, the surface at which the primary transverse beam is to be reflected, and the location of the volume to be inspected.

The receiver transducer means is positioned and oriented for optimal detection of reflections from a defect of both the primary and secondary longitudinal beams. Snell's law can be used to calculate a suitable receiver position. However, in general, some empirical investigation is required for optimization. Theoretical and empirical considerations can also be applied to the emitter location.

Once the emitter and receiver are properly positioned, the emitter can be activated, at step 12. The receiver output is then monitored. The distance the primary longitudinal beam travels to the inspection area is less than the combined distance travelled by the primary transverse beam and the secondary longitudinal beam. Accordingly, detection of a reflection of the primary longitudinal beam at step 13A will precede detection of a reflection of the secondary longitudinal beam at step 13B. In general, the timevarying receiver output voltage is recorded for later analysis.

Generally, the entire volume must be inspected to confirm defect detections and to obtain defect signatures that permit defect characterization. The generation of successive pulses is preferably automated, with the transducers being stepped in unison along a predetermined path. Thus, steps 11-13 are iterated until the path is completed, as indicated by the test at step 14.

Once all the data is collected, it can be analyzed at step 15 to provide the desired location and characterization of defects.

Figure 2:
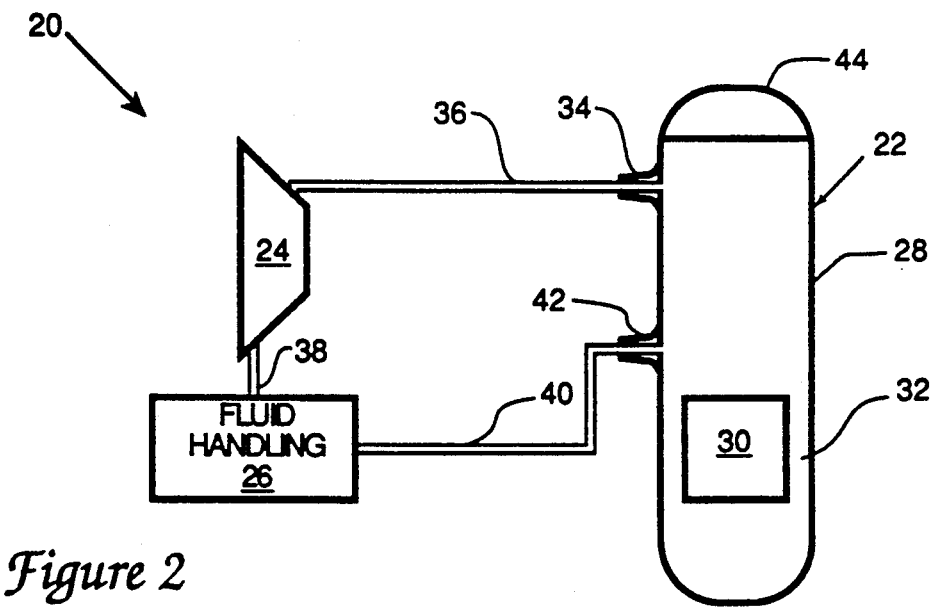
FIG. 2 is a schematic sectional view of a typical reactor system to which the method of FIG. 1 is applied.

Method 10 has proved particularly suited to the inspection of reactor nozzles, such as those in a boiling water reactor system 20, shown in FIG. 2. Reactor system 20 includes a reactor 22, a turbine 24, and a fluid handling system 26. Reactor 22 includes a reactor vessel 28 that confines recirculating water and a core 30 for generating heat. Core 30 boils some of the water circulating therethrough, generating steam. The resulting steam/water mixture rises through core 30. Liquid water is recirculated through a downcomer 32 to reenter core 30 from below. Steam rises from core 30 and exits vessel 28 through a steam exit nozzle 34 and a main steam line 36 to turbine 24. Turbine 24 drives a generator (not shown) to produce electricity. The steam driving turbine 24 condenses and is delivered to fluid handling system 26 via a water line 38. Water is then returned to vessel 28 via feedwater line 40 and feedwater nozzle 42.

Feedwater nozzle 42 is a particular challenge for routine reactor inspection. Because it is relatively hot and is potentially exposed to relatively cool feedwater, nozzle 42 can be subjected to thermal stresses that fatigue and crack its inner surface. Provisions, such as a protective sleeve, are made to minimize the thermal stresses, but the potential for defects remains.

Since it is the interior surface of nozzle 42 that is most subject to thermal stresses and defects, it would be desirable to inspect the interior surfaces directly. Access to the nozzle interior can be achieved by removing vessel top 44. However, this increases potential radiation exposure. Inspection of internal components (many not shown) in the lower reaches of vessel 28 is complicated by intervening components and increased radiation near core 30, and the presence of water submerging core 30. Other nozzles, such as main steam nozzle 34, are more accessible, but it is still safer and more convenient to inspect them without removing vessel top 44.

Figure 3:
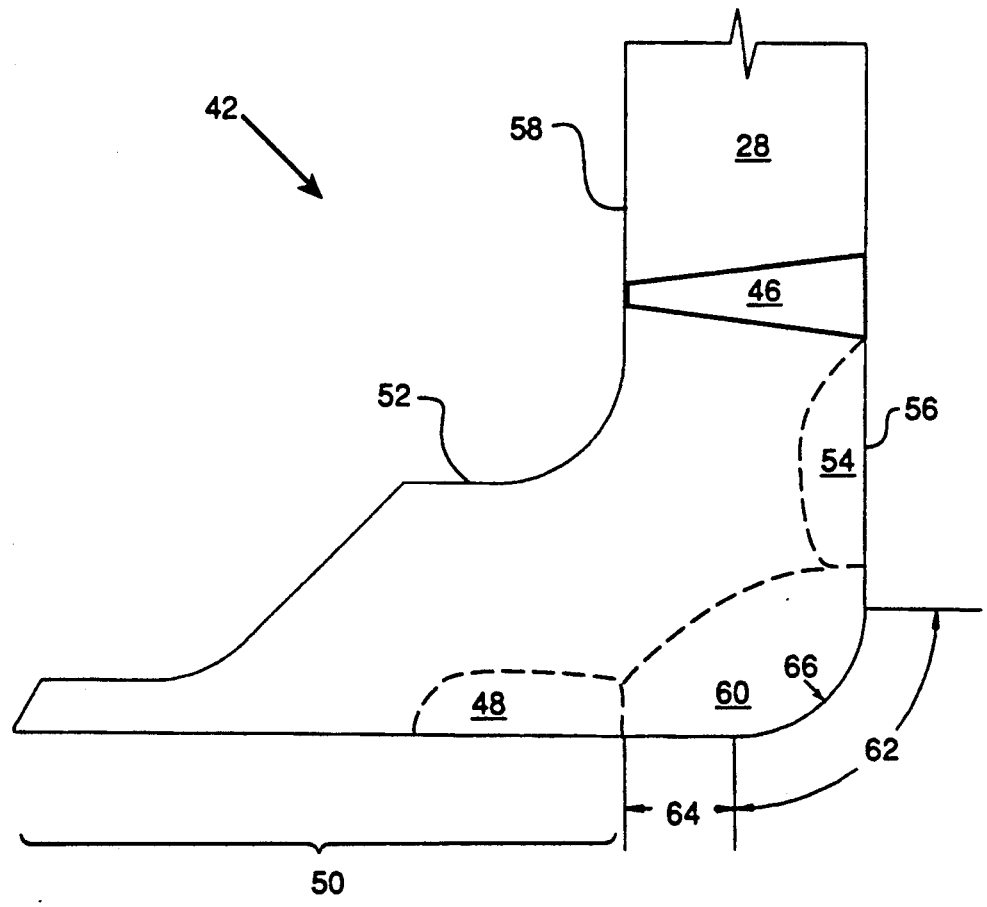
FIG. 3 is a half sectional view taken along a r-z plane of a nozzle of the reactor of FIG. 2 to which the present invention is applied, where the z coordinate is along the nozzle axis and the r coordinate is radial.

The challenges of external ultrasonic inspection of nozzle geometry are discussed vis-a-vis feedwater nozzle 42 with reference to FIG. 3 et seq. Nozzle 42 is attached to vessel 28 via a circular weld 46, which generally has a wedge-shaped cross section. Conventional ultrasound techniques are developed for inspecting the volume adjacent an interior wall from a parallel exterior wall. Thus a volume 48 of a bore 50 of nozzle 42 can be inspected from exterior bore wall 52. Likewise a volume 54 adjacent the interior flare 56 of nozzle 42 can be inspected by placing transducers on an exterior surface 58 of vessel wall 28. Problematically, comparable access is not available for a volume 60 adjacent an inner radius 62 and an adjacent bore extent 64. Accordingly, it can be difficult to detect and characterize a defect 66 in volume 60.

Figure 4:
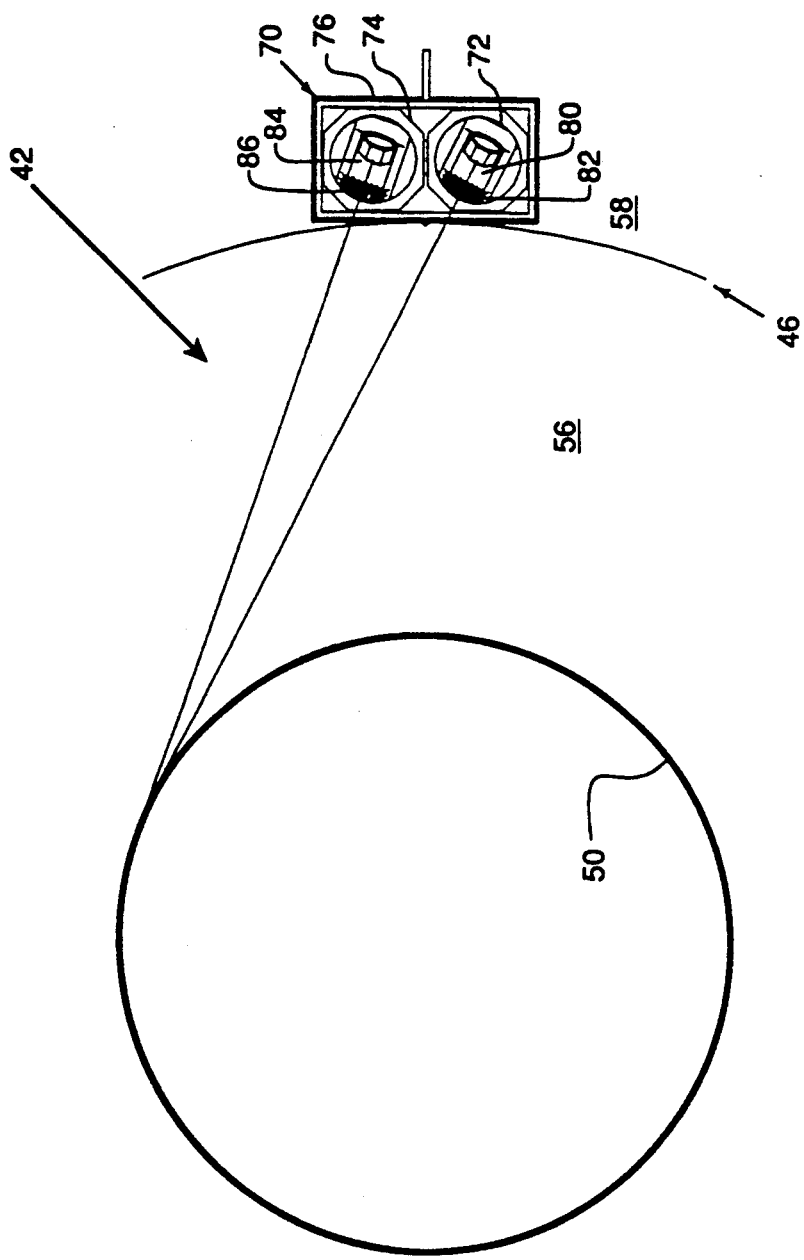
FIG. 4 is sectional view taken along a $\theta$-z plane of the nozzle of FIG. 3, where the $\theta$ coordinate is circumferential.

Method 10 permits volume 60 to be inspected using transducers mounted on exterior surface 58 of vessel 28. Transducer positioning is illustrated in FIG. 4. An inspection assembly 70 holds an emitter assembly 72 and a receiver assembly 74 in predetermined relative positions within a frame 76. Emitter assembly 72 comprises an emitter transducer 80 and an "emitter" lucite wedge 82, which fixes the angle of emitter transducer 80 when mounted on a surface. Receiver assembly 74 similarly comprises a receiver transducer 84 and a "receiver" lucite wedge 86.

The centers of transducers 80 and 84 are about 4" apart for nozzle 42 which has a bore inner diameter of 12", a bore outer diameter of 26", and a flare diameter (and weld inner diameter) of 34". Emitter transducer 80 is oriented so that the primary longitudinal beam is directed at an angle of 24° relative to the radial direction midway between transducers 80 and 84. Receiver transducer 84 is oriented at an 8° angle relative to the same radial direction to optimally receive from the same area targeted by emitter transducer 80.

Both wedges 82 and 86 support a 26.3° inclination between their respective transducers and the normal to vessel wall 58. This angle through lucite wedges corresponds to a primary longitudinal direction about 70° and a primary transverse direction of about 30° in the steel vessel volume. A couplant, oil or water, joins each transducer to its lucite wedge to prevent air pockets, which would attenuate the beam. Similarly, water couples the lucite wedges to the vessel wall.

Figure 5:
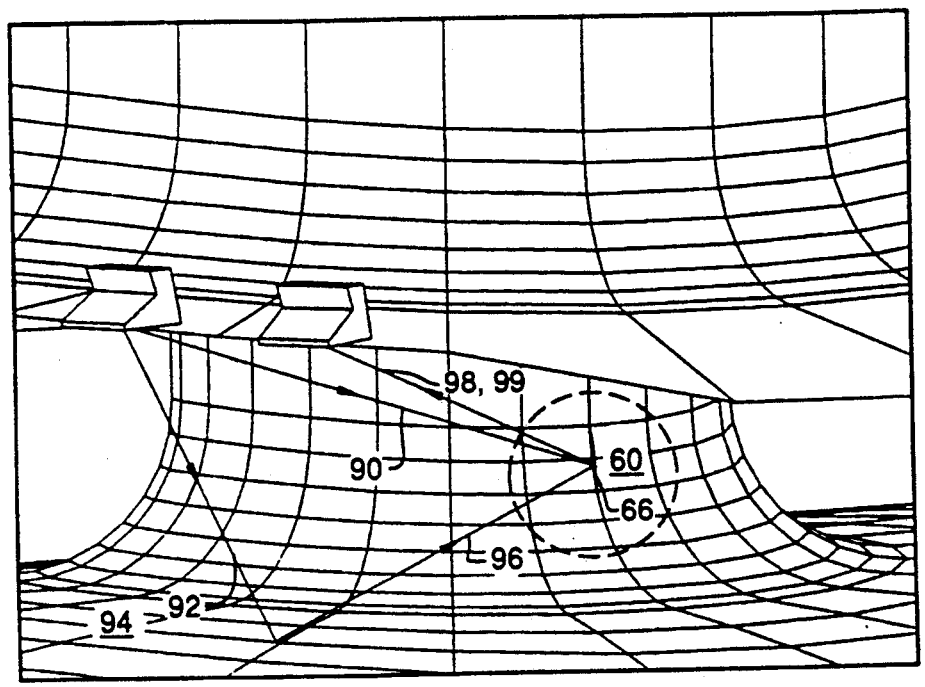
FIG. 5 is a schematic wire-frame view of the nozzle of FIG. 3 illustrating beam paths followed using the method of FIG. 1.

The beam paths of interest are best illustrated in FIG. 5. Primary longitudinal beam 90 is directed toward inspection volume 60. Primary transverse beam 92 impinges on interior wall 94 of vessel 28 at approximately a 30° angle. At this angle, most of the energy of primary transverse beam 92 is converted to a secondary longitudinal beam 96, at approximately a 60° angle relative to the normal to interior vessel surface 94 and toward inspection volume 60. In effect, the present invention provides a virtual transducer at the (interior) point where the secondary longitudinal beam is created.

Figure 6:
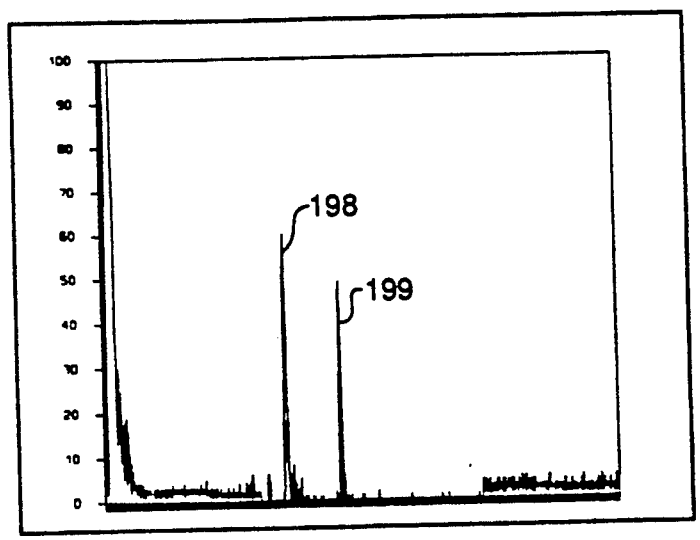
FIG. 6 is a graph illustrating a typical detection signal when a defect is detected using the method of FIG. 1.

Defect 66 in inspection region 60 generates a reflection 98 of the primary longitudinal beam 90 and then a reflection 99 of the second longitudinal beam 96. Reflections 98 and 99 are detected in succession by receiver assembly 74, which outputs respective signal peaks 198 and 199, shown in the rectified voltage x time graph of FIG. 6. Note in FIG. 5 that longitudinal beams 90 and 96 impinge on defect 66 from very different angles. While a defect could be oriented so that it fails to provide a significant reflection of one of the longitudinal beams, it is much less likely that a defect could fail to provide a detectable reflection from at least one of the two longitudinal beams. In general, defects will produce reflections from both longitudinal beams, providing additional characterization from each pulse of the emitter transducer.

The present invention provides a substantial improvement over conventional ultrasound techniques relying on solitary transverse beams for detection, but only for some geometries. These geometries, however, are not limited to nozzles. Other geometries are provided for, as can be determined from Snell's law and other relevant principles. Materials must be considered as the difference in velocities between transverse and longitudinal beams determines in part the geometries amenable to the present invention. The applicability of the present invention can be extended where surfaces are deliberately fabricated to provide the required secondary longitudinal beam. The invention provides for the use of different transducers. In some geometries, the emitter and receiver functions can be performed by the same transducer. The invention provides for spacing the emitter and the receiver at distances other than that described in the preferred embodiments. The emitter can be fixed while the receiver is moved, or the receiver can be fixed while the emitter is moved. In the latter case, step 11B of the method is in effect practiced before step 11A. Other coupling fluids are provided for, as is the coupling of the transducer directly with a fluid, e.g., without a wedge, and controlling the angle with a precision rotating mechanism. These and other modifications to and variations upon the described embodiments are provided by the present invention, the scope of which is limited only by the following claims.

We claim:

1. A method for ultrasonic detection of a defect in an inspection volume of a material body, said method comprising the steps of:
    positioning and orienting transducer means including emitter means and receiver means so as to define
        a first path within said body, said first path consisting of
            a first leg from said emitter means to said defect, and
            a second leg from said defect to said receiver means, and
        a second path within said body, said second path consisting of
            a first leg from said emitter means to a surface,
            a second leg from said surface to said defect, and
            a third leg from said defect to said receiver means,
    activating said emitter means so as to produce
        a primary longitudinal wave along said first leg of said first path, and
        a transverse wave along said first leg of said second path that is mode converted by said surface so as to yield a secondary longitudinal wave along said second leg of said second path;
    detecting at said receiver means a primary reflection, said primary reflection being a reflection of said primary longitudinal wave and traveling along said second leg of said first path; and
    detecting at said receiver means a secondary reflection, said secondary reflection being a reflection of said secondary longitudinal wave and traveling along said third leg of said second path.

2. A method as recited in claim 1 wherein the angle of incidence of said transverse wave on said surface is between 25° and 35° from the normal.

3. A method as recited in claim 2 wherein said inspection volume is part of a nozzle of a nuclear reactor.

4. A method as recited in claim 3 wherein said positioning step involves positioning said transducer means on a reactor pressure vessel section to which said nozzle is welded and wherein said inspection volume is adjacent to the interior of said reactor pressure vessel.

5. A method as recited in claim 1 wherein said emitter means and said receiver means utilize a common transducer.

6. A method as recited in claim 1 wherein said emitter means and said receiver means utilize separate transducers respectively for emitting and receiving ultrasonic waves.

* * * * *